(12) United States Patent
Höfling et al.

(10) Patent No.: US 8,959,935 B2
(45) Date of Patent: Feb. 24, 2015

(54) FREEZING MICROTOME AND METHOD FOR PRODUCING MICROSCOPABLE THIN SECTIONS

(75) Inventors: Uwe Höfling, Ettenheim (DE); Hermann Ulbrich, Bad Schönborn (DE); Ralf Eckert, Schriesheim (DE); Michael Eberhard, Rheingönheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 1327 days.

(21) Appl. No.: 12/761,428

(22) Filed: Apr. 16, 2010

(65) Prior Publication Data

US 2010/0263390 A1 Oct. 21, 2010

(30) Foreign Application Priority Data

Apr. 17, 2009 (DE) .......................... 10 2009 017 848

(51) Int. Cl.
 *F25D 17/02* (2006.01)
 *G01N 1/06* (2006.01)
 *G01N 1/42* (2006.01)

(52) U.S. Cl.
 CPC ... *G01N 1/06* (2013.01); *G01N 1/42* (2013.01)
 USPC ................................................ 62/64; 62/373

(58) Field of Classification Search
 USPC ................ 62/64, 373, 434, 99, 320, DIG. 10; 600/562–572
 See application file for complete search history.

(56) References Cited

U.S. PATENT DOCUMENTS

| | | | | |
|---|---|---|---|---|
| 3,236,133 A * | 2/1966 | De Pas | ............................ | 83/170 |
| 3,605,551 A * | 9/1971 | Steward | ........................ | 409/131 |
| 3,649,108 A * | 3/1972 | Ahrens et al. | .................... | 352/84 |
| 4,121,012 A * | 10/1978 | Bockno | ........................ | 428/369 |
| 4,284,894 A | 8/1981 | Sitte et al. | | |
| 5,048,300 A * | 9/1991 | Lihl | .............. | 62/48.1 |
| 6,416,713 B1 * | 7/2002 | Ford et al. | ....................... | 422/63 |
| 6,615,592 B2 | 9/2003 | Prien et al. | | |
| 2006/0196631 A1 * | 9/2006 | Small et al. | ..................... | 165/10 |

(Continued)

FOREIGN PATENT DOCUMENTS

| | | |
|---|---|---|
| CN | 1538160 A | 10/2004 |
| DE | 1234045 B | 2/1967 |

(Continued)

OTHER PUBLICATIONS

United Kingdom Office Action, Jul. 20, 2010, in UK Application No. GB1006233.9.

(Continued)

*Primary Examiner* — Cheryl J Tyler
*Assistant Examiner* — David Teitelbaum
(74) *Attorney, Agent, or Firm* — Hodgson Russ LLP (57) ABSTRACT

A freezing microtome for the production of microscopable thin sections of tissue samples (60), comprising a cooling device (24, 34, 36, 38, 40, 42, 46, 48, 50, 52) for freezing the tissue samples (60), a cutting device for cutting the frozen tissue samples (60) and a working chamber, in which the cutting device and at least a part of the cooling device (24, 34, 36, 38, 40, 42, 46, 48, 50, 52) are arranged is described. The part of the cooling device (24, 34, 36, 38, 40, 42, 46, 48, 50, 52) arranged in the working chamber contains a liquid coolant (70), in which the tissue samples (60) can be inserted for freezing.

9 Claims, 7 Drawing Sheets

(56) References Cited

U.S. PATENT DOCUMENTS

2007/0137451 A1* 6/2007 Dorenkamp et al. ............ 83/78
2008/0041069 A1   2/2008 Vicar et al.

FOREIGN PATENT DOCUMENTS

| | | | |
|---|---|---|---|
| EP | 1800104 | A1 | 3/2006 |
| EP | 1967836 | A1 | 9/2008 |
| GB | 1152987 | | 5/1969 |
| GB | 1204546 | A | 9/1970 |
| JP | 6088347 | | 5/1985 |
| JP | H01127292 | A | 5/1989 |
| JP | H10111219 | A | 4/1998 |
| JP | H10300644 | A | 11/1998 |
| JP | H11337461 | A | 12/1999 |
| JP | 2004317515 | A | 11/2004 |
| JP | 2004354390 | A | 12/2004 |
| JP | 2006145539 | A | 6/2006 |

OTHER PUBLICATIONS

Schmitt, P., Technik der Gefriermikrotomie, Leitz—Mitt. Wiss. Techn. 8 (3/4) 96-100, 1982, Germany.

* cited by examiner

FREEZING MICROTOME AND METHOD FOR PRODUCING MICROSCOPABLE THIN SECTIONS

CROSS REFERENCE TO RELATED APPLICATIONS

This application claims priority of the German patent application 10 2009 017 848.1 filed Apr. 17, 2009, the entire disclosure of which is incorporated by reference herein.

FIELD OF THE INVENTION

The invention relates to a freezing microtome and a method for the production of microscopable thin sections of tissue samples. In particular, the invention relates to a freezing microtome comprising a cooling device for freezing the tissue samples, a cutting device for cutting the frozen tissue samples and a working chamber, in which the cutting device and at least a part of the cooling device are arranged.

BACKGROUND OF THE INVENTION

By means of freezing microtomes of the aforementioned type thin section specimens are produced from tissue samples, which are subsequently observed under a microscope for diagnostic purposes. For this, the tissue samples are firstly frozen in a cooling device, also referred to as cryostat, and then cut by means of a cutting device. The cooling device and the cutting device are arranged together in a working chamber of the freezing microtome.

The cooling device usually comprises freezing ribs cooled by means of Peltier elements, to which slides holding the tissue samples are attached. This type of sample cooling has the disadvantage that during the freezing process elongated ice crystals are formed in the tissue due to the crystallization of the cellular and extracellular water, which perforate the cells and united cell structures of the tissue and affect the histomorphology adversely. Such tissue damages are also referred to as freezing artifacts. A possible adverse affect by freezing artifacts consists e.g. of the damaged cells releasing endogenous enzymes, which become active during an RNA preparation and thus degrade the substrate used in the preparation. This reduces the sample quality and as a consequence makes a reliable diagnosis more difficult.

To prevent freezing artifacts, it is alternatively suggested to freeze the tissue samples externally, i.e. outside of a microtome, directly by means of liquid nitrogen or by using nitrogen-cooled isopentane. However, the use of liquid nitrogen is complex and expensive. Further, freezing of the tissue samples outside of the microtome involves the risk to mix up the tissue samples.

Regarding prior art, it is further referred to U.S. Pat. No. 6,615,592 B2. Therein a cooling device is described, wherein a liquid coolant is led over the tissue samples to freeze them.

SUMMARY OF THE INVENTION

It is the object of the invention to provide a freezing microtome of the aforementioned type as well as a method for the production of microscopable thin sections of tissue samples which allow for an easy handling of the tissue samples while largely avoiding freezing artifacts.

The invention solves this object with respect to the freezing microtome by the subject-matter of claim 1.

The invention provides the integration of a liquid coolant, which according to latest findings allows a freezing of tissue samples while largely avoiding freezing artifacts, in a freezing microtome. As both the liquid coolant and the cutting device are arranged in the working chamber of the freezing microtome, an easy handling of the tissue samples for the thin section preparation is guaranteed.

For freezing the tissue samples, the liquid coolant preferably has a temperature within a range from approximately −60° C. to 0° C. Further, it preferably has a specific heat capacity within a range from approximately 1.6 to 3.5 kJ/kg·K. Thus it has turned out that if a liquid coolant with these characteristics is used, the cellular and extracellular water when the tissue is frozen only forms small, spherical ice crystals which neither damage the cells nor the cell walls. Thus the native histomorphology remains largely preserved during freezing. This preservation of the morphology facilitates the so-called instantaneous section diagnosis for the pathologist. As the cells and united cell structures are largely preserved and thus the aforementioned endogenous, degrading enzymes are virtually not released, e.g. also very unstable mRNA molecules can be extracted in relative high concentrations. As these information molecules gain in importance regarding the diagnosis of e.g. cancer, the use of a liquid coolant of the aforementioned type promises a significant progress regarding the diagnosis.

Preferably, the cooling device includes a tank arranged in the working chamber for receiving the liquid coolant and the tissue samples. The tank arranged in the working chamber allows for various embodiments of the inventive freezing microtome. In a particularly simple embodiment the liquid coolant is e.g. cooled externally, i.e. outside of the microtome, and then inserted into the tank. In order to simplify the handling it is however advantageous, if the coolant is cooled in the freezing microtome itself.

For this, the cooling device can e.g. include a compression refrigerating machine for cooling the liquid coolant, which works with compression and expansion elements as well as with heat exchangers to implement a thermodynamic cycle.

Preferably, the compression refrigerating machine includes an evaporator arranged in the tank. This evaporator is e.g. formed from a tube, in which a refrigerant such as e.g. R404a evaporates and thus extracts warmth from the liquid coolant, which surrounds the tube in the tank.

In a further advantageous embodiment the compression refrigerating machine includes at least a further evaporator, which is arranged in the working chamber outside of the tank. This further evaporator can e.g. be arranged such that it provides for an air cooling in the working chamber.

The freezing microtome can also be designed such that the cooling device includes a flow-through device having a reservoir for storing the liquid coolant, a cooling aggregate for cooling the coolant stored in the reservoir and a circulation pump, which delivers the liquid coolant via an inflow from the reservoir into the tank and via an outflow from the tank back into the reservoir. This flow-through device can be provided alternatively or additionally to the aforementioned compression refrigerating machine. In the latter case the cooling aggregate causes e.g. a precooling of the coolant stored in the reservoir, while the compression refrigerating machine provides for a cooling of the coolant in the tank.

The freezing microtome has a rinsing device arranged in the working chamber for rinsing the tissue samples frozen by means of the liquid coolant with a cooled rinsing liquid. If the tissue samples are wrapped in protective covers to prevent cross-contaminations of the tissue samples via the coolant, the coolant adhering to the protective covers can be removed by means of the rinsing device before the tissue samples are supplied to the cutting device together with the protective covers.

Preferably, the rinsing device includes a rinsing tank containing the rinsing liquid, which is arranged near the part of the cooling device arranged in the working chamber. By this arrangement of the rinsing tank a contamination of the cutting device by the coolant adhering to the protective covers of the tissue samples can be prevented. As rinsing liquid e.g. diluted or undiluted ethanol or isopropanol can be used.

Further it is advantageous to cool the rinsing liquid as well. For this, in the working chamber a distinct cooling device associated with the rinsing device can be provided. Alternatively, the cooling device determined for cooling the liquid coolant can also be used for cooling the rinsing liquid. When using a compression refrigerating machine, this can e.g. be caused by an additional evaporator arranged in the rinsing tank.

Preferably, the cooled rinsing liquid has a temperature which is approximately equal to the temperature of the liquid coolant. Thus it is assured that the tissue samples also still during the rinsing process keep a temperature, which proved to be optimal with respect to the prevention of freezing artifacts. In particular, the tissue samples do not thaw during rinsing, whereby cutting the tissue samples would be impeded.

According to a further aspect of the invention a method for the production of microscopable thin sections of tissue samples according to claim 11 is provided.

Preferably, the tissue samples are respectively wrapped in a protective cover before being inserted into the liquid coolant. As protective cover e.g. a plastic hose can be used. The protective cover prevents that the coolant comes into direct contact with the tissue sample. Cross contaminations via the liquid coolant can thus be prevented.

The tissue samples can be cut together with the protective covers, in which they have been wrapped before being inserted into the liquid coolant. This facilitates the implementation of the method.

The implementation of the method is further facilitated in that the respective tissue sample is attached to a mounting device before being inserted into the liquid coolant and inserted into the liquid coolant and removed from the liquid coolant after freezing together with the mounting device.

BRIEF DESCRIPTION OF THE DRAWING VIEWS

The invention will be explained in more detail in the following on the basis of embodiments with reference to the Figures, wherein.

DETAILED DESCRIPTION OF THE INVENTION

Figure 1:
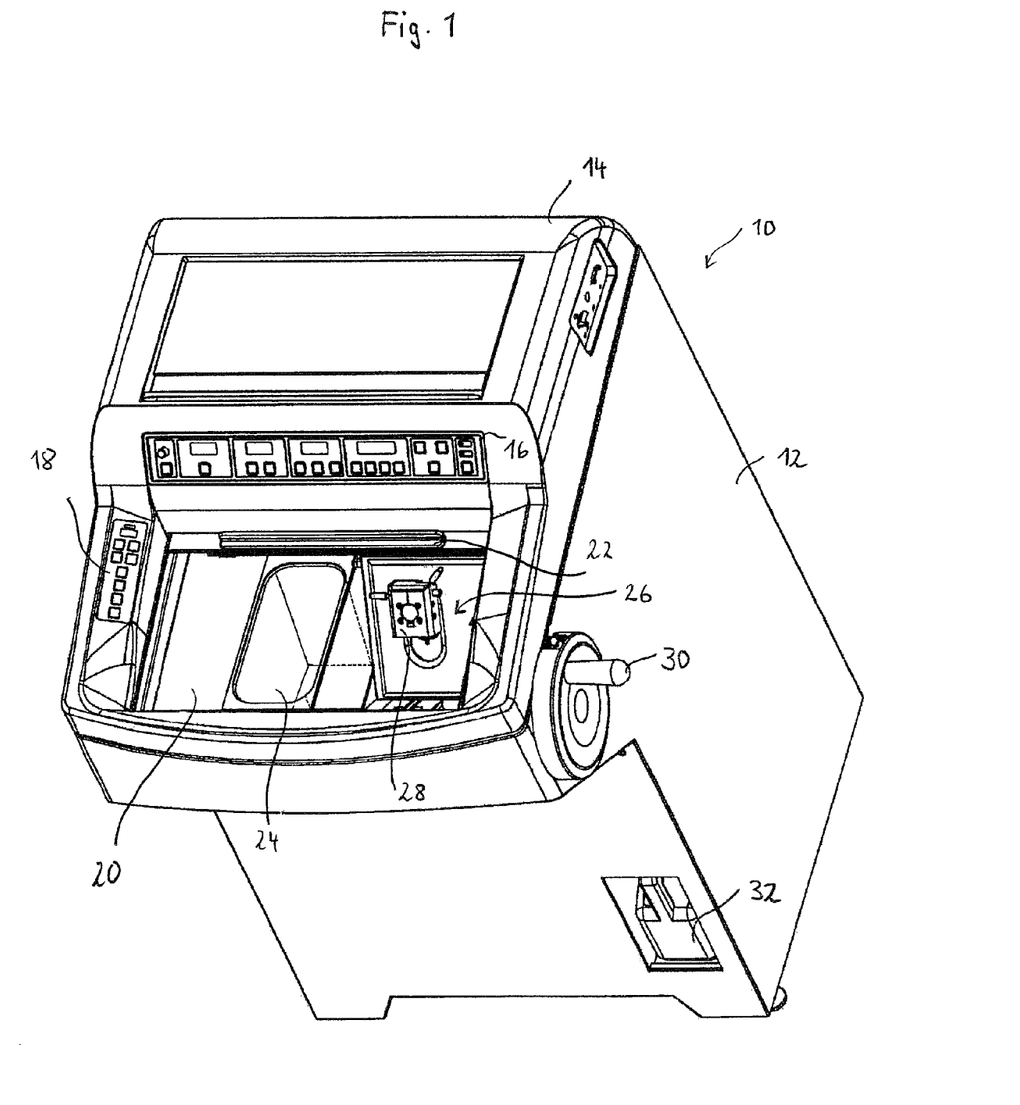
FIG. 1 shows a perspective view of an inventive freezing microtome according to a first embodiment.

FIG. 1 shows a freezing microtome 10 according to a first embodiment. The freezing microtome 10 has a cabinet casing 12, on which a console 14 is mounted. Control panels 16 and 18 with buttons and display elements are on the console 14, via which buttons and display elements an operator can control the operation of the freezing microtome 10.

The freezing microtome 10 has a working chamber 20 with a movable cover 22. In FIG. 1 the cover 22 is inserted and thus the working chamber 20 is open. In the working chamber 20 a tank 24 and a cutting device 26 are arranged. When the freezing microtome 10 operates, the tank 24 contains a liquid coolant not shown in FIG. 1. Tissue samples are inserted into the coolant, the temperature of which is within a range from approximately −60° C. to 0° C. By means of the coolant the tissue samples are frozen and thus hardened. Then, from the hardened tissue samples thin sections can be produced by means of the cutting device 26.

The cutting device 26 comprises a clamping device 28 and a knife facing the clamping device 28, which is not shown in FIG. 1. A slide, which holds a tissue sample, can be attached to the clamping device 28. The clamping device 28 can be approached to the knife facing it. If the clamping device 28 is approached to the knife, thin sections can be planed off from the frozen tissue sample by moving the clamping device 28 upward and downward together with the tissue sample. This upward and downward movement of the clamping device 28 can be caused manually via a handwheel 30 or motor-driven.

In FIG. 1, further a collection tank 32 for condensate is shown, which is arranged at the front side of the cabinet casing 12.

In FIG. 2, again the freezing microtome 10 according to FIG. 1 is shown.

Figure 2:
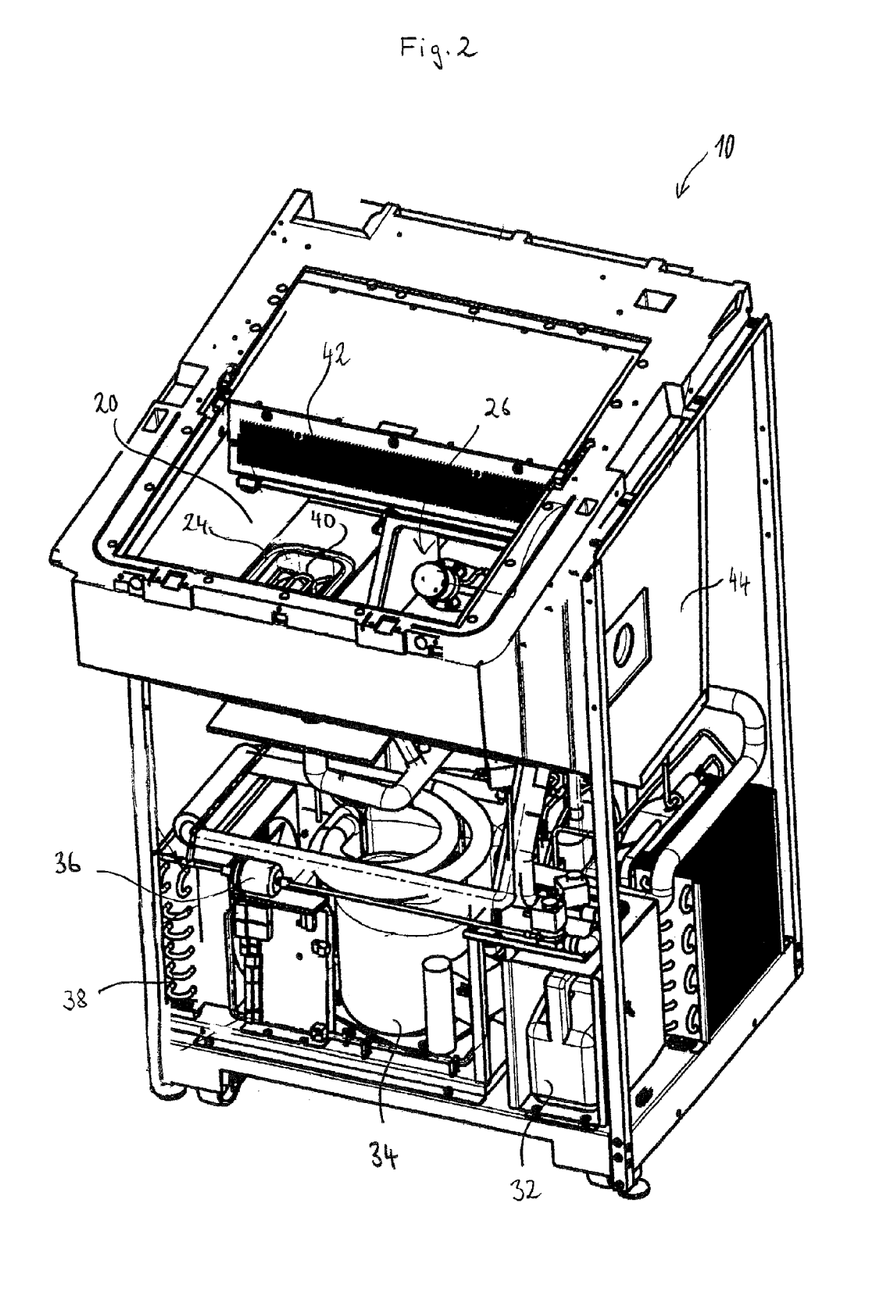
FIG. 2 shows a perspective view of the freezing microtome according to FIG. 1, wherein parts of the freezing microtome are omitted.

Whereby in FIG. 2 some parts of the freezing microtome 10, in particular the side walls of the cabinet casing 12 and the console 14 are omitted to show parts of a cooling device, which is used in the first embodiment.

This cooling device comprises apart from the tank 22 shown in FIG. 1 inter alia a compressor 34, a collection dryer 36, a condenser 38, a tubular evaporator 40, a lamella evaporator 42 and a wall evaporator, which is arranged in a side wall 44 of the working chamber 20, e.g. foamed in place, and therefore cannot be seen in FIG. 2.

The compressor 34, the collection dryer 36 and the condenser 38 are located in the lower part of the cabinet casing 12 below the working chamber 20. The tubular evaporator 40 is arranged in the tank 24. The lamella evaporator 42 is arranged in the working chamber 20 outside of the tank 24. The cooling device comprises further components such as tubes, temperature sensors and expansion valves, which are not further identified in FIG. 2.

With reference to the schematic illustration according to FIG. 3, in the following the refrigeration cycle of the cooling device used in the freezing microtome 10 is described.

The cooling device works with a refrigerant such as e.g. R404a. The pressure ratios are selected in the refrigeration cycle such that the evaporating temperature of the refrigerant in this embodiment is between approximately −40° C. to −50° C.

In the compressor 34 the refrigerant present in the vaporous state of aggregation is compressed and thus heated up. The hot refrigerant vapor is then cooled down in the condenser 38 so far that it condenses. Subsequently, the liquid refrigerant flows through the collection dryer 36. The collection dryer 36 has on the one hand the function to receive and store the liquid refrigerant. On the other hand, it has the function to dehumidify the liquid refrigerant to prevent icing of various components of the refrigeration cycle, e.g. of the tubular evaporator 40 and the lamella evaporator 42.

Figure 3:
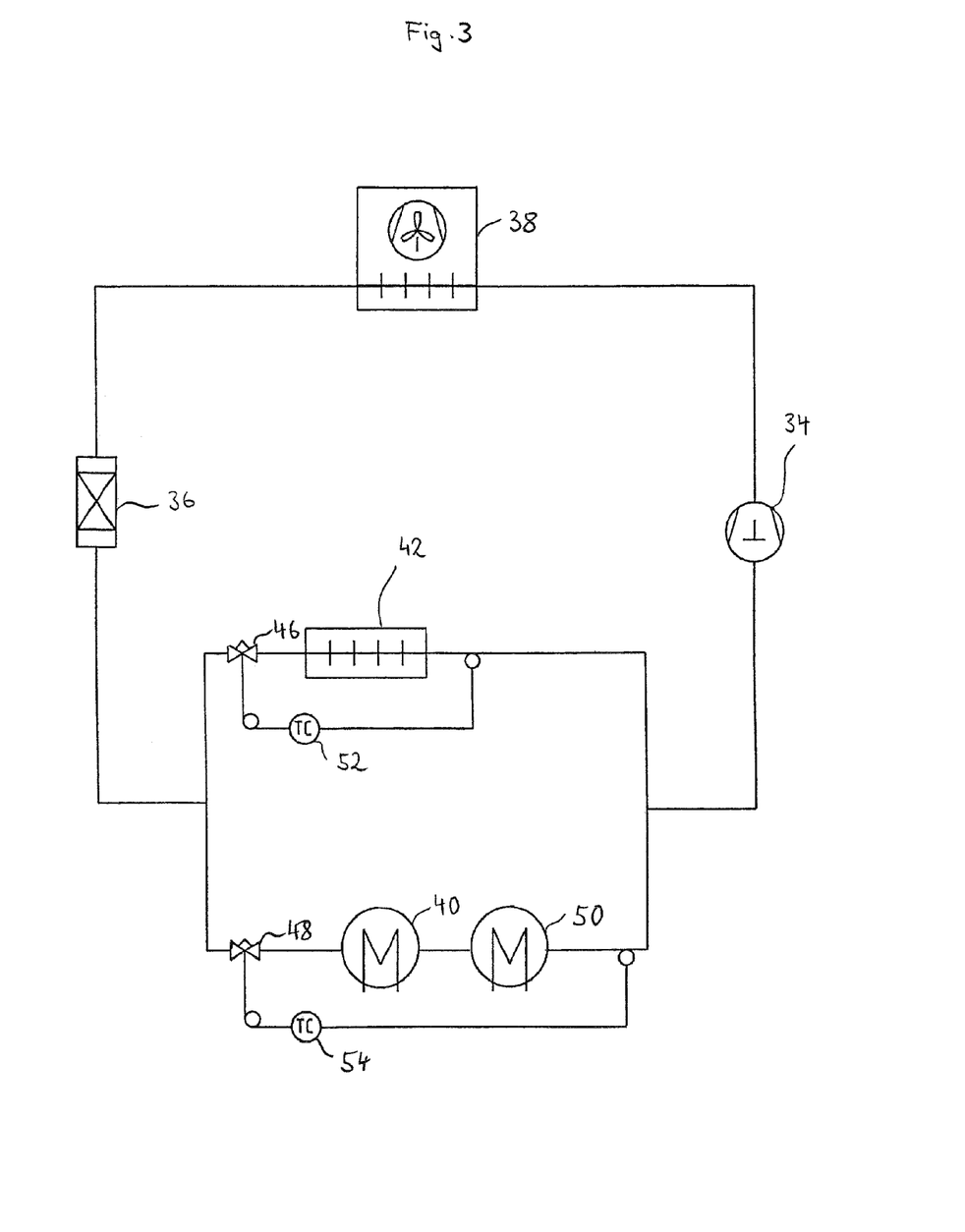
FIG. 3 shows a schematic illustration of a refrigeration cycle provided in the freezing microtome according to FIGS. 1 and 2.

The liquid refrigerant then flows on the one hand via a first expansion valve 46 into the lamella evaporator 42 arranged in the working chamber 20 outside of the tank 24 and on the other hand via a second expansion valve 48 into the tubular evaporator 40 arranged in the tank 24 and into the wall evaporator arranged in the side wall 44 of the working chamber 20, which wall evaporator is referred to with 50 in FIG. 3. In the branch of the refrigeration cycle, wherein the lamella evaporator 42 is located, a first overheating sensor 52 is provided. Correspondingly, a second overheating sensor 54 is provided in the branch of the refrigeration cycle, wherein the tubular evaporator 40 and the wall evaporator 50 are arranged.

The expansion valves 46 and 48 reduce the pressure of the liquid refrigerant flowing therethrough. In the evaporators 40, 42 and 50 the refrigerant evaporating due to the pressure drop extracts evaporation heat from the medium, in which the respective vaporizer 40, 42 or 50 is located. In this manner, the liquid coolant, which surrounds the tubular evaporator 40 in the tank 24 as well as the air, which surrounds the lamella evaporator 42 and the wall evaporator 50 in the working chamber 20, are cooled down.

Eventually, the refrigerant vapor is sucked in by the compressor 34 and again compressed, whereupon the refrigeration cycle starts anew.

Figure 4:
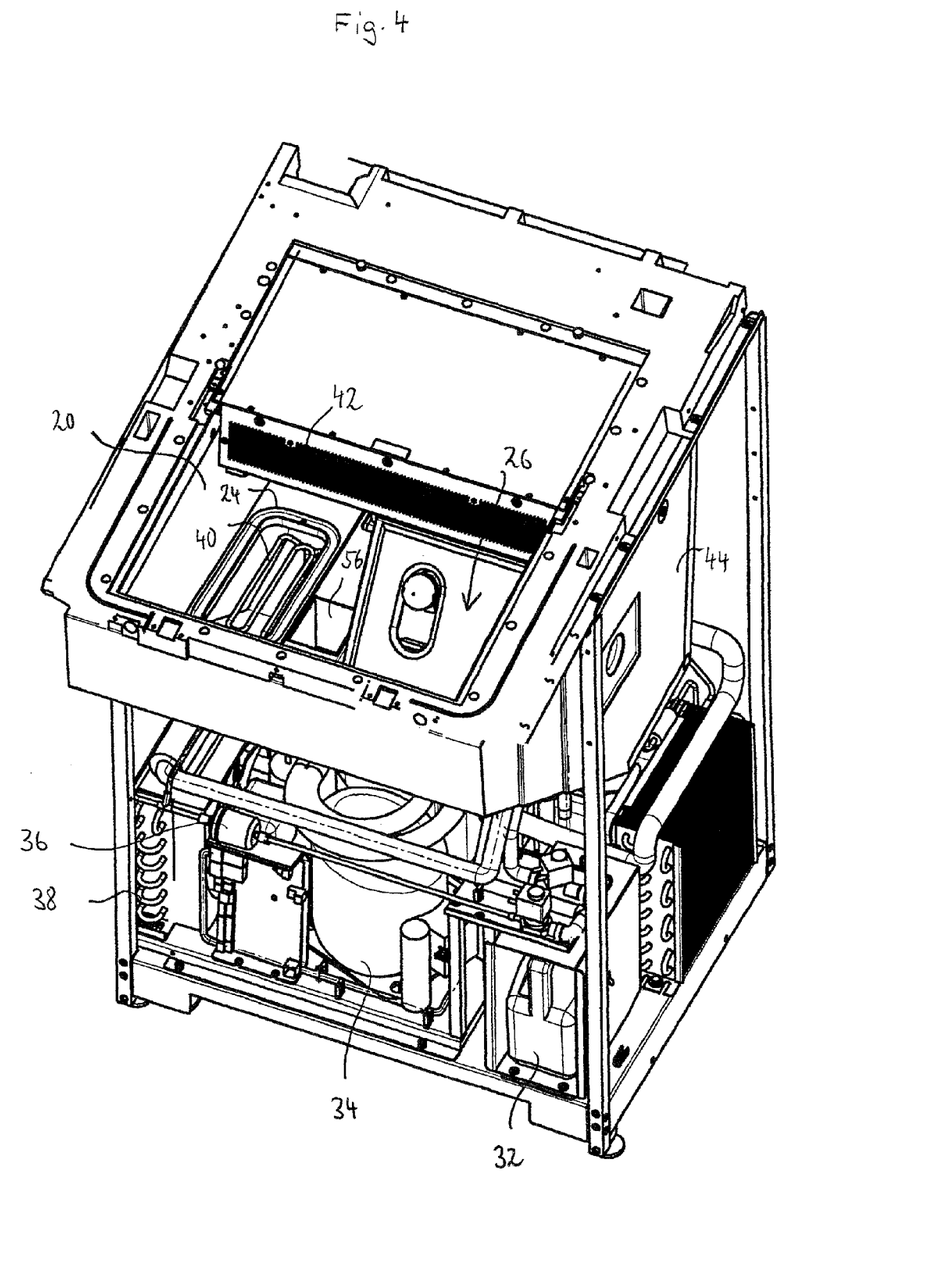
FIG. 4 shows a perspective view of an inventive freezing microtome according to a second embodiment, wherein parts of the freezing microtome are omitted.

In FIG. 4, a second embodiment is shown, wherein a rinsing device is additionally provided in the working chamber 20. Apart from this rinsing device the second embodiment is identical to the first embodiment.

In the second embodiment the rinsing device is simply designed as rinsing tank 56. A rinsing liquid, e.g. ethanol, can be filled into the rinsing tank 56, in which the tissue samples, after they have been frozen in the liquid coolant and have been taken out of the tank 24, can be purified.

Figure 5:
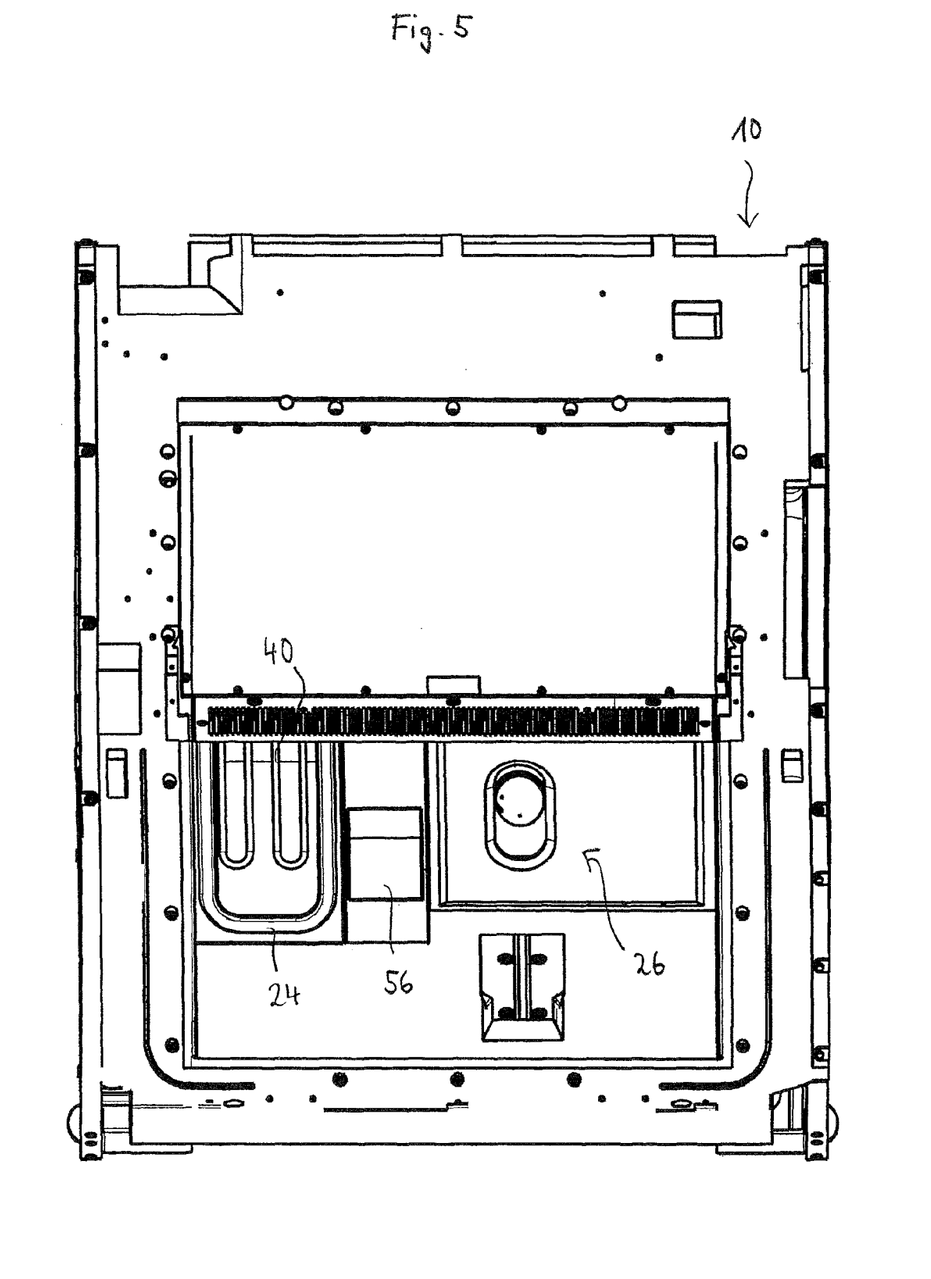
FIG. 5 shows a top view of the freezing microtome according to FIG. 4.

As the top view according to FIG. 5 also shows, the rinsing tank 56 is arranged in the working chamber 20 between the tank 24 and the cutting device 26. In particular, the rinsing tank 56 is located in immediate proximity of the tank 24. Thus it is assured that the working chamber 20 is not contaminated with the liquid coolant, if the operator takes the frozen tissue samples out of the tank 24.

Preferably, the rinsing liquid contained in the rinsing tank 56 is cooled. This can e.g. be caused by a further evaporator, not shown in FIGS. 4 and 5. Such an evaporator could e.g. be designed according to the tubular evaporator 40 arranged in the tank 24. The temperature to which the rinsing liquid is cooled, is in this embodiment approximately identical to the temperature of the liquid coolant.

In the above described embodiments the liquid coolant is simply filled into the tank 24. However, this simple design is to be understood only as an example. Thus, it is e.g. also possible to transfer the liquid coolant in a cycle from a liquid reservoir, which is located inside the cabinet casing 12, via an inflow into the tank 24 and via an outflow from the tank 24 back into the liquid reservoir. To this end, a circulation pump can be provided in the freezing microtome 10 which pumps the liquid coolant into the tank 24 and out of the tank 24.

A corresponding cycle can also be provided for the rinsing liquid contained in the rinsing tank 56. In this case, a liquid reservoir for the rinsing liquid, a circulation pump as well as an inflow and an outflow for the rinsing tank 56 are to be provided in the freezing microtome 10.

Figure 6A:
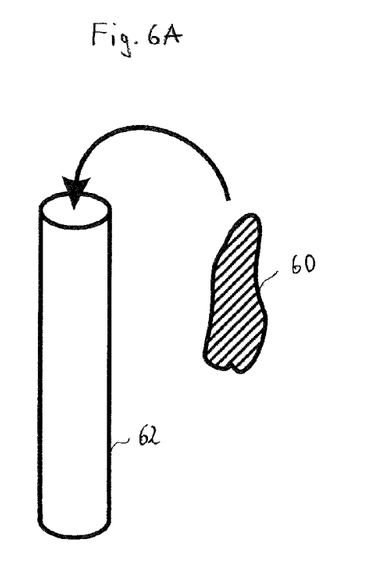
FIGS. 6A, 6B and 6C show schematic illustrations showing how a tissue sample is wrapped in and inserted into the liquid coolant.
Figure 6B:
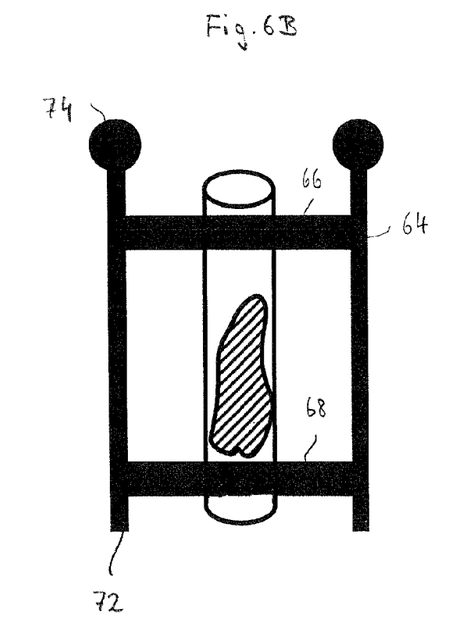
Figure 6C:
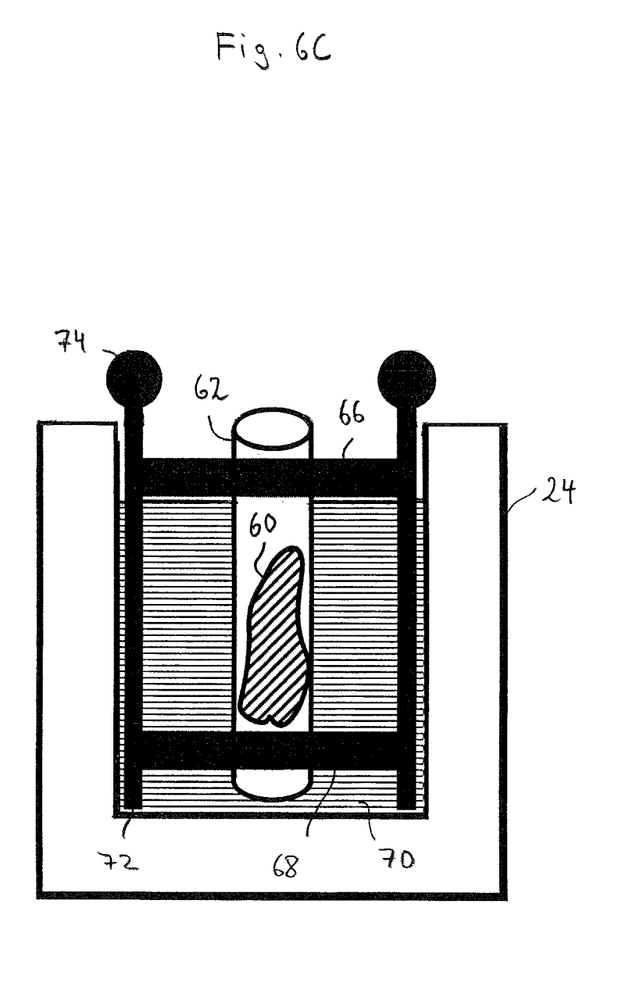

With reference to FIGS. 6A, 6B and 6C in the following it shall be illustrated by way of example, how microscopable thin sections of tissue samples are produced by means of the freezing microtome 10.

As shown in FIG. 6A, first a tissue sample identified with 60 is put into a protective cover 62, which is simply designed as plastic hose in the present embodiment. The protective cover 62 is clamped in a mounting device 64 shown in FIG. 6B together with the tissue sample 60 contained therein. Thereby the protective cover 62 can e.g. be clamped such that the ends thereof being open at first are pressed together and thus closed by clamping arms 66, 68 arranged pairwise respectively, which are formed at the mounting device 64 and of which in the side views according to FIGS. 6B and 6C only respectively one clamping arm 66 or 68 is shown. In FIGS. 6B and 6C this is only schematically indicated.

The mounting device 64 is then placed in the tank 24 together with the protective cover 62 held thereon, in which the liquid coolant indicated with 70 in FIG. 6C is located.

In the present embodiment the mounting device 64 is designed such that it can simply be placed in the tank 24 and removed therefrom by the operator. For this, the mounting device 64 has feet 72, with which it is placed on the bottom of the tank 24. Further the mounting device 64 has handholds 74, which project from the liquid coolant 70, when the mounting device 64 is placed in the tank 24. The operator can thus simply take the mounting device 64 out of the liquid coolant 70 at the handholds 74.

After the tissue sample 60 has been frozen in the liquid coolant 70, it is supplied to the cutting device 26 together with the mounting device 64 to produce the desired thin sections.

LIST OF REFERENCE SIGNS 10 freezing microtome
12 cabinet casing
14 console
16, 18 control panels
20 working chamber
22 cover
24 tank
26 cutting device
28 clamping device
30 handwheel
32 collection tank
34 compressor
36 collection dryer
38 condenser
40 tubular evaporator
42 lamella evaporator
44 side wall
46, 48 expansion valves
50 wall evaporator
52, 54 overheating sensor
56 rinsing tank
60 tissue sample
62 protective cover
64 mounting device
66, 68 clamping arms
70 coolant
72 feet
74 handholds

What is claimed is:
1. A freezing microtome for the production of microscopable thin sections of tissue samples, comprising:

a cooling device for freezing the tissue samples (60), the cooling device comprising a tank configured to contain liquid coolant;

a refrigerating machine comprising an evaporator, the evaporator being disposed in the tank;

a cutting device for cutting the frozen tissue samples;

a working chamber in which the cutting device and at least a part of the cooling device are arranged, wherein the tank is arranged in the working chamber for receiving the liquid coolant into which the tissue samples are insertable for freezing the tissue samples;

a rinsing device arranged in the working chamber (20) for rinsing the frozen tissue samples with a cooled rinsing liquid, the rinsing device comprising a rinsing tank; and an additional evaporator in the rinsing tank configured to cool the cooled rinsing liquid.

2. The freezing microtome according to claim 1, wherein the liquid coolant has a temperature within a range from approximately −60° C. to 0° C. for freezing the tissue samples.

3. The freezing microtome according to claim 1, wherein the liquid coolant has a specific heat capacity within a range from 1.6 to 3.5 kJ/kg·K.

4. The freezing microtome according to claim 1, wherein the refrigerating machine comprises a compression refrigerating machine for cooling the liquid coolant.

5. The freezing microtome according to claim 4, wherein the compression refrigerating machine includes a further evaporator arranged in the working chamber outside of the tank.

6. The freezing microtome according to claim 4, further comprising a cabinet casing including an upper part and a lower part, wherein the working chamber is arranged in the upper part of the cabinet casing, and wherein the compression refrigerating machine includes a compressor arranged in the lower part of the cabinet casing.

7. The freezing microtome according claim 1, wherein the cooling device includes a flow-through device having a reservoir for storing the liquid coolant, a cooling aggregate for cooling the liquid coolant stored in the reservoir, and a circulation pump which delivers the liquid coolant via an inflow from the reservoir into the tank and via an outflow from the tank back into the reservoir.

8. The freezing microtome according to claim 1, wherein the rinsing device is arranged near the part of the cooling device arranged in the working chamber.

9. The freezing microtome according to claim 8, wherein the temperature of the rinsing liquid is adjusted to a temperature which is approximately equal to the temperature of the liquid coolant.

\* \* \* \* \*